US010319474B1

(12) United States Patent
Cave et al.

(10) Patent No.: US 10,319,474 B1
(45) Date of Patent: Jun. 11, 2019

(54) METHOD AND SYSTEM FOR PRODUCING STATISTICAL ANALYSIS OF MEDICAL CARE INFORMATION

(71) Applicant: Cave Consulting Group, Inc., San Mateo, CA (US)

(72) Inventors: Douglas G Cave, San Mateo, CA (US); Yuri Alexandrian, San Ramon, CA (US); John T Calvin, Mountain View, CA (US); Jenine A Lara, San Francisco, CA (US)

(73) Assignee: Cave Consulting Group, Inc., San Mateo, CA (US)

( * ) Notice: Subject to any disclaimer, the term of this patent is extended or adjusted under 35 U.S.C. 154(b) by 0 days.

(21) Appl. No.: 14/266,842

(22) Filed: May 1, 2014

Related U.S. Application Data

(63) Continuation of application No. 13/621,222, filed on Sep. 15, 2012, now Pat. No. 8,751,263, which is a continuation of application No. 12/473,147, filed on May 27, 2009, now Pat. No. 8,301,464.
(Continued)

(51) Int. Cl.
*G16H 40/20* (2018.01)
(52) U.S. Cl.
CPC .................. *G16H 40/20* (2018.01)
(58) Field of Classification Search
CPC ........ G06Q 50/22; G06Q 50/24; G06Q 10/10; G06Q 10/04; G06Q 30/02; G16H 40/20;
(Continued)

(56) References Cited

U.S. PATENT DOCUMENTS 4,489,387 A 12/1984 Lamb et al.
4,491,725 A 1/1985 Pritchard
(Continued)

OTHER PUBLICATIONS

S. Anderson et al., "The Gatekeeper Effect on Managing Acute Medical Conditions," Medical Interface, pp. 122-129, Sep. 1996.
(Continued)

*Primary Examiner* — Joseph D Burgess
(74) *Attorney, Agent, or Firm* — Armstrong Teasdale LLP

(57) ABSTRACT

A method and system for producing statistical analysis of medical care information comprises: aggregating medical care providers to a peer group level; aggregating medical care information at the peer group level and at the medical care provider level; computing a statistical analysis, such as performing Pearson's correlation analysis; and generating peer group level and medical care provider level results utilizing the computed statistical analysis. Also, a method for producing statistical analysis of medical care information for a medical care provider efficiency measurement comprises: applying minimum unit of analysis criteria for medical care providers to be used in statistical analysis; calculating an overall weighted average medical care information measure for each medical care provider; calculating a medical condition-specific medical care information measure for each medical care provider; removing outlier medical care providers from statistical analysis at medical care information level; calculating a statistical analysis to medical care provider efficiency measurement at each medical care information level using a statistical calculation; and selecting statistically related medical care information to identify medical care providers meeting a desired practice pattern.

14 Claims, 9 Drawing Sheets

Related U.S. Application Data

(60) Provisional application No. 61/082,080, filed on Jul. 18, 2008.

(58) Field of Classification Search
CPC ........ G16H 10/20; G16H 10/60; G06F 19/00; G06F 19/324; G06F 19/328; G06F 19/3481
See application file for complete search history.

(56) References Cited

U.S. PATENT DOCUMENTS

| | | | |
|---|---|---|---|
| 4,667,292 | A | 5/1987 | Mohlenbrock et al. |
| 4,858,121 | A | 8/1989 | Barber et al. |
| 4,878,175 | A | 10/1989 | Norden-Paul et al. |
| 4,937,743 | A | 6/1990 | Rassman et al. |
| 4,987,538 | A | 1/1991 | Johnson et al. |
| 5,001,630 | A | 3/1991 | Wiltfong |
| 5,018,067 | A | 5/1991 | Mohlenbrock et al. |
| 5,065,315 | A | 11/1991 | Garcia |
| 5,070,452 | A | 12/1991 | Doyle, Jr. et al. |
| 5,072,383 | A | 12/1991 | Brimm et al. |
| 5,099,424 | A | 3/1992 | Schneiderman |
| 5,225,976 | A | 7/1993 | Tawil |
| 5,235,702 | A | 8/1993 | Miller |
| 5,253,164 | A | 10/1993 | Holloway et al. |
| 5,301,105 | A | 4/1994 | Cummings, Jr. |
| 5,307,262 | A | 4/1994 | Ertel |
| 5,319,543 | A | 6/1994 | Wilhelm |
| 5,324,077 | A | 6/1994 | Kessler et al. |
| 5,325,293 | A | 6/1994 | Dome |
| 5,359,509 | A | 10/1994 | Little et al. |
| 5,365,425 | A | 11/1994 | Torma et al. |
| 5,392,209 | A | 2/1995 | Eason et al. |
| 5,404,292 | A | 4/1995 | Hendrickson |
| 5,467,268 | A | 11/1995 | Sisley et al. |
| 5,471,382 | A | 11/1995 | Tallman et al. |
| 5,483,443 | A | 1/1996 | Milstein et al. |
| 5,486,999 | A | 1/1996 | Mebane |
| 5,519,607 | A | 5/1996 | Tawil |
| 5,557,514 | A * | 9/1996 | Seare .................... G06Q 40/02 705/2 |
| 5,583,758 | A | 12/1996 | McIlroy et al. |
| 5,664,207 | A | 9/1997 | Crumpler et al. |
| 5,724,379 | A | 3/1998 | Perkins et al. |
| 5,835,897 | A | 11/1998 | Dang |
| 5,970,463 | A | 10/1999 | Cave et al. |
| 6,223,164 | B1 | 4/2001 | Seare et al. |
| 2004/0111291 | A1 | 6/2004 | Dust et al. |
| 2007/0106533 | A1* | 5/2007 | Greene .................. G06Q 10/10 705/2 |

OTHER PUBLICATIONS

H. Beckman et al., "Current Approaches to Improving the Value of Care: A Physician's Perspective," The Commonwealth Fund, 46 pages, Nov. 2007.

S. Bronskill, "Longitudinal profiles of health care providers," Statistics in Medicine, vol. 21, pp. 1067-1088, 2002 (no month).

D. Cave et al., "Analyzing Patterns-of-Treatment Data to Provide Feedback to Physicians," Medical Interface, pp. 117-128, Jul. 1994.

D. Cave, "Analyzing the content of physicians' medical practices," J. Ambulatory Care Manage, vol. 17, No. 3, pp. 15-36, Jul. 1994.

D. Cave, "Pattern-of-Treatment Differences Among Primary Care Physicians in Alternative Systems of Care," Benefits Quarterly, pp. 6-19, Third Quarter 1994.

D. Cave, "Profiling Physician Practice Patterns Using Diagnostic Episode Clusters," Medical Care, vol. 33, No. 5, pp. 463-486, May 1995.

D. Cave, et al. "Who Treats Medical Conditions More Cost Efficiently?," Medical Interface, pp. 136-142, May 1994.

D. Cave, "Small-area variations in the treatment of prevalent medical conditions: A comparison of three cities in the Northeast," J Ambulatory Care Manage, 18(3), pp. 42-57, 1995.

J. Chilingerian, "Evaluating physician efficiency in hospitals: A multivariate analysis of best practices," European Journal of Operational Research, pp. 278-574, 1995.

E. Fisher et al ., The Implications of Regional Variations in Medicare Spending. Part 1: The Content, Quality, and Accessibility of Care, Annals of Internal Medicine, 138, 39 pages, 2003.

R. Greene et al., "Beyond the Efficiency Index: Finding a Better Way to Reduce Overuse and Increase Efficiency in Physician Care," DataWatch, pp. 250-259, May 20, 2008.

R. Greene et al., "Increasing Adherence to a Community-Based Guideline for Acute Sinusitis through Education, Physician Profiling, and Financial Incentives," American Journal of Managed Care, vol. 10, No. 10, pp. 670-678, Oct. 2004.

E. Guadagnoli et al., "Variation in the Use of Cardiac Procedures After Acute Myocardial Infarction," NEJM vol. 333, No. 9, pp. 573-578, Aug. 31, 1995.

T. Hofer et al., "The Unreliability of Individual Physician "Report Cards" for Assessing the Costs and Quality of Care of a Chronic Disease," JAMA, vol. 281, No. 22, pp. 2098-2105, Jun. 9, 1999.

M. Hornbrook et al., "Health Care Episodes: Definition, Measurement, and Use," Medical Care Review, vol. 42, No. 2, pp. 163-218, Fall 1985.

D. Ko et al., "Regional Differences in Process of Care and Outcomes for Older Acute Myocardial Infarction Patients in the United States and Ontario, Canada," Journal of the American Heart Association, Circulation 2007: 115, pp. 196-203, 2007.

F. L. Lucas et al., "Temporal Trends in the Utilization of Diagnostic Testing and Treatments for Cardiovascular Disease in the The United States, 1993-2001," Circulation 113(3), 12 pages, Jan. 24, 2006.

F. Mullan, "Wrestling with Variation: An Interview with Jack Wennberg," Health Affairs—Web exclusive, pp. 73-80, Oct. 2004.

D. Salkever et al., "Episode-Based Efficiency Comparisons for Physicians and Nurse Practitioners," Medical Care, vol. XX, No. 2, pp. 143-153, Feb. 1982.

R. Schneeweiss et al., "Diagnosis Clusters Adapted for ICD-9-CM and ICHPPC-2", The Journal of Family Practice, vol. 22, No. 1, pp. 69-72, 1986 (no month).

R. Schneeweiss et al., "Diagnosis Clusters: A New Tool for Analyzing the Content of Ambulatory Medical Care," Medical Care, vol. XXI, No. 1, pp. 105-122, Jan. 1983.

T. Stukel et al., Analysis of Observational Studies in the Presence of Treatment Selection Bias: Effects of Invasive Cardiac Management on AMI Survival Using Propensity Score and Instrumental Variable Methods, JAMA 297(3), 17 pages, Jan. 17, 2007.

T. Stukel et al., "Long-term Outcomes of Regional Variations in Intensity of Invasive vs Medical Management of Medicare Patients With Acute Myocardial Infarction," JAMA 293 (11), pp. 1329-1337, Mar. 16, 2005.

B. Surovich, et al., "Discretionary Decision Making by Primary Care Physicians and the Cost of U.S. Health Care," National Institute of Health, 27(3), pp. 813-823, Jun. 24, 2008.

J. Thomas et al, "Identifying "Practice Efficiency" Outliers Among Primary Care Physicians: Effects of Risk Adjustment Methodology and Practice Efficiency Metric," Report to the Robert Woods Johnson Foundation Health Care Financing and Organization (HCFO) Program, HFCO Grant # 36874, Blue Cross Blue Shield of Michigan Foundation Grant #243-II/99, 20 pages, Mar. 18, 2003.

J. Weinstein, "United States' Trends and Regional Variations in Lumbar Spine Surgery: 1992-2003," Spine vol. 31, No. 23, pp. 2707-2714, Nov. 23, 2006.

W. Welch et al., "Geographic Variation in Expenditures for Physicians' Services in the United States," The New England Journal of Medicine, vol. 328, No. 9, pp. 621-627, Mar. 1994.

J. Wennberg, "Unwarranted variations in healthcare delivery: implications for academic medical centres," BMJ, vol. 325, pp. 961-964, Oct. 26, 2002.

* cited by examiner

Marketbasket: General Internists
SOI - Medical Condition: 1 - Low back pain

Aggregate Group: 1
Correlation Cutoff: 0.05

NOTE: Screenings, vaccinations, and other preventive services may appear in certain medical conditions due to physician practice and coding patterns.

Correlation Report | Clear All MedMarkers

Service Category | Sub-Service Category | Sub-Service Detail

Service Detail Correlation Report

Print

| | Corr | Service | Description | Sub-Service Category | Number Services | Services per Episode | Charge per Service | Unique Practitioners | Performing Practitioners |
|---|------|---------|-------------|----------------------|-----------------|----------------------|--------------------|-----------------------|--------------------------|
| ☐ | 0.49 | 72148 | mri lumbar spine w/o dye | Imaging | 27 | 0.043 | $165 | 93 | 18.3% |
| ☐ | 0.40 | 85025 | complete cbc w/auto diff wbc | Lab | 45 | 0.071 | $9 | 93 | 18.3% |
| ☐ | 0.39 | 80061 | lipid panel | Lab | 54 | 0.085 | $13 | 93 | 29.0% |
| ☐ | 0.37 | 99283 | emergency dept visit | Professional Visits | 23 | 0.037 | $104 | 93 | 18.3% |
| ☐ | 0.36 | 84443 | assay thyroid stim hormone | Lab | 12 | 0.019 | $13 | 93 | 8.6% |
| ☐ | 0.33 | 80053 | comprehen metabolic panel | Lab | 47 | 0.074 | $11 | 93 | 26.9% |
| ☐ | 0.28 | 81000 | urinalysis, nonauto w/scope | Lab | 70 | 0.110 | $4 | 93 | 31.2% |
| ☐ | 0.25 | 71020 | chest x-ray | Imaging | 19 | 0.030 | $28 | 93 | 11.8% |
| ☐ | 0.23 | 99213 | office/outpatient visit, est 15 | Professional Visits | 505 | 0.813 | $52 | 93 | 96.8% |
| ☐ | 0.23 | 72110 | x-ray exam of lower spine | Imaging | 73 | 0.115 | $32 | 93 | 36.6% |
| ☐ | 0.22 | 72070 | x-ray exam of thoratic spine | Imaging | 13 | 0.021 | $21 | 93 | 6.5% |
| ☐ | 0.22 | 99243 | office consultation 40 | Professional Visits | 8 | 0.013 | $135 | 93 | 4.3% |
| ☐ | 0.21 | 97014 | electric stimulation therapy | Physical Therapy | 14 | 0.023 | $11 | 93 | 6.5% |

FIG. 3

MedMarker Checkout Report

| Corr | Service | Service or Sub - Service Category | Description | Number Services | Services per Episode | Charge per Service | Unique Practitioners | Performing Practitioners |
|---|---|---|---|---|---|---|---|---|
| 0.49 | 72148 | Imaging | mri lumbar spine w/o dye | 27 | 0.043 | $165 | 93 | 18.3% |
| 0.23 | 72110 | Imaging | x-ray exam of lower spine | 73 | 0.115 | $32 | 93 | 36.6% |
| 0.23 | 99213 | Professional Visits | office/outpatient visit, est 15 | 505 | 0.813 | $52 | 93 | 96.8% |

[Print]

FIG. 4

MedMarker Target Report

| Practitioner ID | Practitioner Name | Practitioner Episodes | Efficiency Score | MedMarkers Meeting Criteria |
|---|---|---|---|---|
| 9ETEXI666PVXFB5 | | 7 | 3.29 | 2/3 |
| G2EWNZ666PZIZFN | | 15 | 3.19 | 2/3 |
| 1YI3XM666PV0496 | | 5 | 2.23 | 2/3 |
| G2ENAX666PVOAMX | | 9 | 2.22 | 3/3 |
| G2JRUS666PROQRP | | 6 | 2.18 | 1/3 |
| G2BEYN666PRSATZ | | 10 | 2.10 | 1/3 |
| 1MBLI9666PIR3NF | | 7 | 2.10 | 3/3 |
| G2BEYN666PRHVWE | | 8 | 1.70 | 3/3 |

[Export] [Print]

Find Practitioners who have at least [1 ▼] out of [3] MedMarkers above with

Services per Episode at least [10% ▼] [greater ▼] than the Peer Group Rate

FIG. 5

Practitioner Efficiency Report

Practitioner Name:
Specialty Type: Dermatologist
Practitioner ID:
Agg Group Name:

Quartile: 4
Decile: 10
→ Efficiency Score: 1.42
Significant Difference: Yes
(P<0.25)

Marketbasket: DERMATOLOGY

*What service category and CPT-4 codes are most correlated to Efficiency Score?*

Average Charge Per Episode of Care

| Medical Condition Name | SOI | Episode Count | Average Charge per Episode | Professional Outpt and Ambulatory | | | | | | Facility | | | Other Med |
|---|---|---|---|---|---|---|---|---|---|---|---|---|---|
| | | | | Prof Visits | Diag Tests | Lab/ Path | Med/ Surg | Rx | Prof Inpt | Outpt | Hosp Inpt | Altern Sites | |
| Peer Group Weighted Avg | — | 33057 | $399 | $83 | $4 | $3 | $103 | $156 | $0 | $7 | $0 | $0 | $7 |
| Practitioner Weighted Avg | — | 174 * | $567 * | $115 | $4 * | $84 * | $132 * | $223 | $0 | $5 | $0 | $0 | $5 |
| Acne | | | | | | | | | | | | | |
| Peer Group | 1 | 3100 | $265 | $88 | $1 | $7 | $14 | $152 | $0 | $0 | $0 | $0 | $2 |
| Practitioner | 1 | 18 * | $470 * | $131 | $0 * | $49 * | $4 * | $286 | $0 | $0 | $0 | $0 | $0 |
| Benign neoplasm of skin | | | | | | | | | | | | | |
| Peer Group | 1 | 8367 | $279 | $65 | $1 | $76 | $90 | $45 | $0 | $1 | $0 | $0 | $2 |
| Practitioner | 1 | 46 * | $776 * | $84 | $2 * | $301 * | $286 * | $84 | $0 | $0 | $0 | $0 * | $19 |
| Dermatitis and eczema | | | | | | | | | | | | | |
| Peer Group | 1 | 3983 | $207 | $82 | $14 | $10 | $21 | $77 | $0 | $0 | $0 | $0 | $3 |
| Practitioner | 1 | 23 * | $385 * | $149 | $14 * | $35 | $17 * | $171 | $0 | $0 | $0 | $0 | $0 |

FIG. 6

Services Prevalence Report

*Practitioner Name:*
*Specialty Type:* Dermatologist
*Practitioner ID:*
*Agg Group Name:*

*Quartile:* 4
*Decile:* 10
*Efficiency Score:* 1.42
*Significant Difference:* Yes
(P<0.25)

*Marketbasket:* DERMATOLOGY
*Medical Condition:* All
*SOI:* All
*Sub-Service Category:* 8 Surgical

|  |  | Practitioner | | | Peer Group | | | |
|---|---|---|---|---|---|---|---|---|
| | | Unique Episodes 174 | | | 33057 | | | |
| | | Unique Practitioner 1 | | | 111 | | | |
| Service | Description | Number Services | Services per Episode | Charge per Service | Number Services | Services per Episode | Charge per Service | Services per Episode Percent Difference From Peer Group |
| 11101 | biopsy, skin add on | 110 | 0.60 | $41.90 | 2189 | 0.066 | $31.08 | 854.7% |
| 11100 | biopsy, skin lesion | 83 | 0.477 | $82.36 | 5796 | 0.175 | $71.26 | 172.1% |
| 11402 | exc tr-ext b9+marg 1.1-2 cm | 35 | 0.201 | $132.60 | 407 | 0.012 | $104.52 | 1533.8% |
| 17003 | destruct premalg les, 2-14 | 18 | 0.103 | $16.22 | 21033 | 0.636 | $10.31 | -83.7% |

Score = 2.73

Correlate to Efficiency Score

| | CPT 11100 | |
|---|---|---|
| Prov ID | Eff Score | CPT Score |
| Derm1 | 1.42 | 2.73 |
| Derm2 | 0.92 | 0.80 |
| Derm3 | 1.10 | 1.05 |

FIG. 7

Procedure Code Report
Dermatology

Medical Condition: All
SOI: All
Sub-Service Category: 8-Surgical

| Correlation | Procedure | Short Name | Count | Avg Rate per Episode | Avg Cost per Proc |
|---|---|---|---|---|---|
| -0.071 | 17000 | destruct premalg lesion | 11,055 | 0.33 | $52.99 |
| 0.289 | 11100 | biopsy, skin lesion | 5,845 | 0.18 | $71.21 |
| 0.218 | 11101 | biopsy, skin add-on | 1,718 | 0.05 | $39.48 |
| -0.133 | 11900 | Injection into skin lesions | 1,344 | 0.04 | $39.82 |
| 0.053 | 11301 | shave skin lesion | 1,012 | 0.03 | $58.62 |
| 0.039 | 11300 | shave skin lesion | 905 | 0.03 | $38.58 |
| -0.148 | 11901 | added skin lesions injection | 579 | 0.02 | $51.30 |
| 0.302 | 11401 | exc tr- extb9+marg 0.6-1 cm | 528 | 0.02 | $94.38 |
| 0.026 | 96900 | ultraviolet light therapy | 528 | 0.02 | $10.57 |
| 0.051 | 11310 | shave skin lesion | 467 | 0.01 | $52.79 |
| 0.221 | 11402 | exc tr- extb9+marg 1.1-2 cm | 402 | 0.01 | $105.46 |
| 0.059 | 17004 | destroy premlg lesions 15+ | 346 | 0.01 | $185.03 |
| 0.085 | 11305 | shave skin lesion | 275 | 0.01 | $40.27 |
| 0.093 | 11400 | exc tr- ext b9+marg 0.5 < cm | 241 | 0.01 | $84.80 |

Number of Physicians = 111

MedMarker:
Build a procedure group around Skin Biopsies
PG=11100 - 11101

FIG. 8

METHOD AND SYSTEM FOR PRODUCING STATISTICAL ANALYSIS OF MEDICAL CARE INFORMATION

CROSS REFERENCE TO RELATED APPLICATIONS

This application is a Continuation of co-pending U.S. patent application Ser. No. 13/621,222, filed Sep. 15, 2012, which is a Continuation of U.S. patent application Ser. No. 12/473,147, filed May 27, 2009, and issued as U.S. Pat. No. 8,301,464 on Oct. 30, 2012, which claims priority to our provisional patent application entitled "METHOD AND SYSTEM FOR ANALYZING PHYSICIAN EFFICIENCY SCORES TO IDENTIFY REASONS FOR INEFFICIENT AND EFFICIENT PRACTICE PATTERNS", with Ser. No. 61/082,080, and filed Jul. 18, 2008, incorporated herein by reference.

FIELD OF THE INVENTION

The present invention generally relates to analyzing health care information and, more specifically, to a system and method of producing statistical analysis of medical care information for a medical care provider efficiency measurement. The method comprises calculating a statistical analysis to medical care provider efficiency measurement at an overall weighted average and at each medical care information level using a statistical calculation; and selecting statistically related medical care information to identify medical care providers meeting a desired practice pattern.

BACKGROUND OF THE INVENTION

Health care costs continue to rise at a rapid rate and total national health expenditures are expected to rise at twice the rate of inflation in 2008. U.S. health care spending is expected to increase at similar levels for the next decade.

One factor contributing to rising health care costs is due to 10% to 20% of physicians, across specialty types, practicing inefficiently. Efficiency means using an appropriate amount of medical resources in an appropriate setting to treat a medical condition or given number of medical conditions, and achieving a desired health outcome and quality of patient care. Thus, efficiency is a function of unit price, volume of service, intensity of service, and quality of service. The inefficient practitioners are often those 10% to 20% of practitioners by specialty type utilizing significantly more services to treat a given grouping of patients with equivalent medical conditions or condition-specific episodes of care as compared to their immediate peer group or best practice guideline. The inefficient practitioners can be responsible for driving 10% to 20% of the unnecessary, excess, medical expenditures incurred by employers and other health care purchasers, equating to billions of dollars nationally.

Currently health plans, insurance companies, third party administrators (TPAs), health maintenance organizations, and other health firms (which collectively shall be called "health plans") expend a significant amount of technical, clinical, and analytical resources trying to identify the inefficient practitioners.

Once health plans have identified inefficient practitioner, they realize that each practitioner has a different practice pattern to deal with and has its own little 'microcosm' of practice. At the microcosm level, many clinical and analytical resources are currently expended trying to determine the microcosm practice patterns for each practitioner for each specialty type. The result is that health plans may end up managing hundreds of different practice patterns which is time and resource intensive and makes monitoring over time difficult.

It is often extremely difficult and costly to identify and target the one or two services most associated with practitioner efficiency. Different practice patterns of each practitioner as well as the inability to easily identify services most associated with practitioner efficiency, make it challenging and costly for health plans to embark on strategies to reduce expenditure and improve quality. Programs such as targeted practitioner education and behavioral change, Pay for Performance (P4P) and value-based benefit plan design become more resource intensive and costly and less effective due to difficulties in knowing where to focus and areas to target for improvements. Additionally, the lack of focus results in challenges in monitoring and measuring improvements over time.

BRIEF SUMMARY OF THE INVENTION

A method and system for producing statistical analysis of medical care information comprises: aggregating medical care providers to a peer group level; aggregating medical care information at the peer group level and at the medical care provider level; computing a statistical analysis, such as performing Pearson's correlation analysis; and generating peer group level and medical care provider level results utilizing the computed statistical analysis.

Also, a method for producing statistical analysis of medical care information for a medical care provider efficiency measurement comprises: applying minimum unit of analysis criteria for medical care providers to be used in statistical analysis; calculating an overall weighted average medical care information measure for each medical care provider; calculating a medical condition-specific medical care information measure for each medical care provider; removing outlier medical care providers from statistical analysis at medical care information level; calculating a statistical analysis to medical care provider efficiency measurement at each medical care information level using a statistical calculation; and selecting statistically related medical care information to identify medical care providers meeting a desired practice pattern.

BRIEF DESCRIPTION OF THE DRAWINGS

FIG. 3 is an exemplary Sub-Service Detail Correlation Report, in accordance with one embodiment of the present invention;

FIG. 4 shows an exemplary MedMarker Checkout Report, in accordance with the embodiment shown in FIG. 3;

FIG. 5 shows a MedMarker Target Report, in accordance with the embodiment shown in FIG. 4;

FIG. 6 is an exemplary Practitioner Efficiency Report, in accordance with one embodiment of the present invention;

FIG. 7 is an exemplary Service Prevalence Report, in accordance with the example shown in FIG. 6;

FIG. 8 is an exemplary Procedure Code Report for one specialty, in accordance with the invention and example shown in FIG. 7;

DETAILED DESCRIPTION OF THE INVENTION

Figure 1:
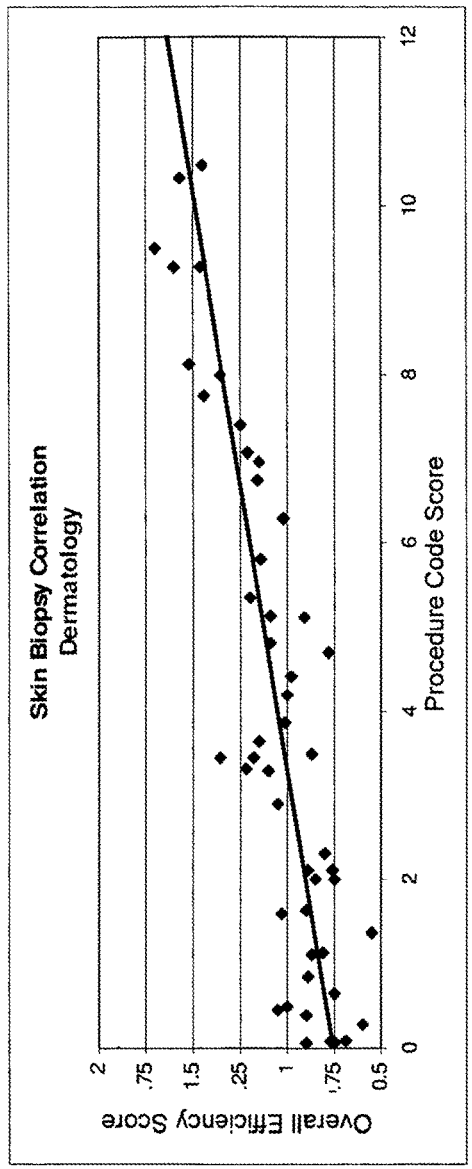
FIG. 1 is a graph showing a Positive Correlation Example.

A Grouper system uses medical care information to build medical condition-specific episodes. Once these condition-specific episodes of care are built, then the episodes are examined through an EfficiencyCare system.

Efficiency means using an appropriate amount of medical resources in an appropriate setting to treat a medical condition or a given number of medical conditions, and achieve a desired quality of patient care. Thus, efficiency is a function of unit price, volume of service, intensity of service, and may include a quality of service component. Volume refers to the number of services performed to treat a specific medical condition (e.g., an office visit, two laboratory tests, and one prescription drug). Intensity refers to the magnitude of medical care ordered to treat a medical condition (e.g., an x-ray versus a computed tomography scan).

The end result there is typically a score between 0.70 and 1.50. This score reflects the resources a health care provider uses in treating a grouping of patients with medical conditions or condition-specific episodes of care as compared to their immediate peer group or a best practice guideline. If a health care provider receives a score of 0.70, then that health care provider is using 30% fewer resources as compared to the peer group.

The Grouper system generates three primary data sets: Assign.tab data set that assigns episodes of care to health care providers; PatientCLI.tab data set that contains patient claim line items (CLI); and EpMaster.tab data set that contains episodes of care information. The EfficiencyCare system utilizes the Assign.tab data set to generate: a Score.tab data set that includes health care provider efficiency scores; a Detail.tab data set that provides health care provider efficiency score details; and an ProvEp.tab data set that provides health care provider efficiency episodes. The present invention primarily involves a BullsEye system that utilizes those data sets described above to generate a BullsEyeMB.tab and BullsEyeMCID.tab data sets that targets medical care information most related to or indicative of health care provider efficiency and inefficiency.

There are three input files to one embodiment of the present invention. One of these input files comes from the Grouper system, and it's called the Patient CLI File 42. This file contains all the claim line items from the CLI Input File, but with the claims organized by medical condition episode of care. In one embodiment, 11 additional pieces of information are added to each claim line item (CLI), and this is the Patient CLI File. These additional pieces of information are added for ease of data mining.

The other two input files for one embodiment of the present invention are output files from EfficiencyCare system. One of these files is the Detail.tab File 68. A record in this file is the health care provider (e.g. physician).

The other file is called the ProvEP.tab File 44, which is an episode file, and it contains all the final episodes of care that made it through EfficiencyCare system and into the Detail.tab file 68. In this embodiment, the ProvEP.tab File 44 is preferred to have because it contains the episode identifiers in this file that allow the present invention to tie back the Claim Line Items (CLIs) in the Patient CLI File.

In one embodiment of the present invention the ProvEP.tab File 44 is used to identify the episode IDs for a health care provider, and it is these episode IDs that are assigned to the health care provider (e.g. physician) and used to calculate his or her efficiency score. Then, the present invention data mines over into the PatientCLI.tab File 42 to find out the CPT-4 codes responsible for a provider's 1.25 or 1.40 efficiency score. That is, determining why the provider is using more or fewer services. However, there are hundreds of potential CPT-4 codes that could be the cause, because a large number of different medical conditions are typically being examined for each health care provider. So, the present invention uses a statistical measure, such as a Pearson's Correlation (a statistic that associates two variables—in this case it is typically the health care provider's efficiency score from EfficiencyCare system (other statistical tools, models, and distributions are also within the scope of this invention)), to a procedure or service (e.g., CPT-4 or HCPCS code) score. The closer to 1.00, the stronger the association (with a Pearson's correlation coefficient). So, the present invention typically reviews large numbers of potential procedure or service (e.g., CPT-4 or HCPCS) codes that could potentially be a primary cause of efficiency or inefficiency, and then determines that a clinical leader should really just focus on a small number (e.g. 2 to 5) of procedure or service codes because these are the procedure or service codes that tend to be most associated with those health care provider's efficiency scores that are high, for example, 1.20 and above, or low. But, also note that these same procedure or service codes identify procedures that efficient providers are doing much less of. Thus, these MedMarkers (i.e., procedures or service codes associated with provider efficiency scores) may also be used to identify efficient health care providers as well. This is why typically MedMarkers are those procedures or services that are associated with provider efficiency scores. And note that health care provider efficiency scoring is preferably done on a specialty by specialty basis, so cardiologists are evaluated separately from general internists and separately from pediatricians.

The present invention "automates" the process for targeting these MedMarkers. That is, analysts at a health plan, physician group, or any other organization might be able to look for these associations by doing a specialized three month study, and then determining the procedures and services (e.g., CPT-4 and HCPCS) associated with the efficiency score of health care providers for a specialty type. This is a long process. The present invention provides software, methods, and algorithms that automate this process, greatly reducing the time needed to find these associations, as well as increasing the accuracy of the results.

After selecting the MedMarkers, the present invention then targets the health care providers that meet the specialty-specific practice pattern as reflected by the MedMarkers selected by a user. It can then present the specified MedMarker results (rates per episode of care) for the health care provider as compared to the selected peer group.

The present invention saves information technology (IT) resources, statistician and analyst resources, and clinical resources needed by a health plan, physician group, or any other organization to identify these important MedMarkers. The process is automated.

Also, once these MedMarkers are known, then the health plan, physician group, or any other organization can take action (i.e., implement strategies that fit each health plan, physician group, or any other organization's philosophies for reducing practice patterns variation) to improve efficiency through working with the health care providers to reduce variability in the identified MedMarkers, focus health care payment reform with respect to the MedMarkers, and implement health plan benefit plan design changes such as adding in deductibles or copayments for the MedMarkers to make the consumer more aware of those services (i.e., MedMarkers) associated with inefficient health care provider practice patterns.

The following personnel in a health plan or physician group can use these MedMarkers to improve medical management performance: medical directors to work with network health care providers to improve performance; health care analysts and informatics specialists that examine claims data to observe reasons for health care provider practice pattern differences or variation; health care actuaries that want to understand services and procedures (i.e., MedMarkers) to target to change health care provider reimbursement to reduce adverse incentives for health care providers to perform more of a certain service or procedure.

One embodiment of the present invention utilizes ASCII tab-delimited database output files from the Grouper system and the EfficiencyCare system. There are the Detail.tab 68, PatientCLI.tab 42, and ProvEP.tab 44 Files. Then, this embodiment, using these input files, produces two intermediate output files, ProvCLI.tab and MinProvEp.tab. These intermediate output files are then used to produce two final output files, BullsEyeMB.tab and BullsEyeMCID.tab. Other file and data structures are also within the scope of the present invention, including databases.

The present invention is the first to use statistical techniques that automates the process for identifying only those procedures and services (e.g., CPT-4 and HCPCS codes) that are most associated with the health care provider efficiency score. One of the unexpected advantages is that the MedMarkers are often unexpected, and sometimes even counterintuitive.

Also, in other embodiments of the present invention:

In the preferred embodiment, only services and procedures are analyzed. However, in another embodiment, drug prescriptions are analyzed in a similar manner.

In another embodiment, there may be a spreadsheet that loads the user identified MedMarkers, the MedMarker service rate per episode, the targeted lower MedMarker rate per episode, the average allowed charge amount for each MedMarker, and the prevalence rate of the medical condition. The spreadsheet can then calculate potential savings for the user using the below formula:

Savings Calculation=Current MedMarker services per episode(−)Target MedMarker services per episode(×)Average allowed charge per service (×)Number of episodes In another embodiment, Service Code Groups are built. In one example, two unique CPT-4 codes for skin biopsy (11100 and 11101) may be examined separately, and therefore, perform a Pearson's correlation on them separately. But, in another embodiment, they are combined together into a specific Service Code Group, which is this case can be called Skin Biopsies=11100+ 11101. The rates per episode would also be combined and the present invention would be run only after Service Code Groups are formed to find MedMarkers. Here are some possible Service Code Groups:

Destruction of Premalignant Lesions=17000+17004 (these are two of several CPT-4 codes corresponding to Destruction of Premalignant Lesions)

Shave Skin Lesions=11300+11301+11305+11310 (these are some of the several CPT-4 codes corresponding to Shave Skin Lesions)

Calculating the Pearson's Correlations, eventually, on Service Code Groups in some situations may result in more meaningful results to a user than just inspecting each CPT-4 code result individually. Note that the CPT-4 codes in a Service Code Group often look very similar in terms of their verbal description—because they are. For example, under the Destruction of Premalignant Lesions, it may be that code 17000 is used for destroying fewer than 15 lesions, and code 17004 is used for billing purposes for destroying more than 15 lesions. One can see on the verbal description for the codes that code 17004 has +15 lesions on it. Thus, these codes are very similar, and sometimes are just volume oriented. Here's another potential Service Code Group:

Upper Gastrointestinal (GI) Endoscopy=43239+43235 (these are two of several CPT-4 codes corresponding to Upper GI Endoscopy), whereby:

43239=Upper GI Endoscopy with biopsy

43239=Upper GI Endoscopy, diagnosis without biopsy

Thus, here, the determination is not made based on numbers, but instead a moderate procedure type difference which is having a biopsy present or not. However, this still would potentially be a good Service Code Group.

One embodiment of the present invention is made up of four components:

The Grouper system groups unique ICD.9 diagnosis codes into 526 meaningful medical conditions based on clinical homogeneity with respect to generating a similar clinical response from health care providers treating a patient.

The EfficiencyCare system is health care provider efficiency measurement software that takes the output from the Grouper system and develops specialty-specific health care provider efficiency scores that compare individual health care provider efficiency against the efficiency of a peer group of interest or practice pattern of interest.

Correlation Calculation Software takes output from the Grouper system and EfficiencyCare system and performs correlation analysis of health care providers' service, sub-service, and procedure or service code scores as compared to their efficiency score.

A Reporting Dashboard, Other Reports, and Open Architecture Output Files. The Reporting Dashboard produces correlation summary reports by service category, sub-service category, and procedures and service code. Reports may include a MedMarker Selection/Summary Report, and Health Care Provider Summary Report. Embodiments of the present invention also provides other reports at key points during processing. All reports are based on output files accessible to the user, and these output files may be used for additional client-developed analysis.

There are several ways that the present invention may be used to add value to an organization. The present invention rapidly targets MedMarkers (i.e., those few procedures and services most associated with health care provider efficiency scores). Knowing these MedMarkers, the present invention identifies health care providers meeting an organization's established MedMarker criteria. On drill-down, the user generally knows the established MedMarker practice patterns per identified health care provider.

Next, users can identify a practice pattern (preferably per specialty type) that identifies inefficient health care providers. Therefore, they may develop and educate their medical management staff on a standard, MedMarker-based, practice pattern. This enables an organization's medical management staff to cost-effectively implement and monitor one standard health care provider feedback program.

Moreover, MedMarkers identified by the present invention identify potential areas of significant procedure and service over-utilization, upcoding, and unbundling. Therefore, MedMarkers may serve as a source for potential health care provider fee payment adjustments by specialty type per region. Here are some examples:

Potential over-utilization example: Dermatologists receiving an inefficient score perform more skin biopsies for the same grouping of medical conditions.

Potential upcoding example: Dermatologists receiving an inefficient score upcode their office visits from 10 minutes to 15-or-20 minutes.

Potential unbundling example: Dermatologists performing a skin biopsy receive payment for both a 20 minute office visit and the skin biopsy, increasing their payment over 300% as compared to a 10 minute office visit alone.

An organization now can have explicit procedures and services to improve its current health care provider payment system by implementing changes to reduce over-utilization, upcoding, and unbundling.

Furthermore, health services research shows that health care provider efficiency measurement methodologies often falsely identify some health care providers as inefficient, when in fact, the health care providers really are efficient ("false positives"). As a result, health care providers may be inappropriately excluded from high performance networks or not receive pay for performance bonuses.

For the first time, organizations can have an automated tool to validate the accuracy of their health care provider efficiency scores. In order for each health care provider's score to be validated as accurate, they can confirm that the health care provider has a higher MedMarker utilization per episode (as compared to the peer group). The end result will typically be higher acceptance of results by network health care providers, thereby reducing potential conflicts, as well as reducing the clinical and analyst resources used to justify the accuracy of each score.

The present invention uses the output from Grouper and EfficiencyCare systems to develop specialty-specific correlations to health care provider efficiency at the:

Service and sub-service category level
Medical condition level
Procedure or service code level, There are several steps to identifying a MedMarker (i.e. a procedure and service correlated to health care provider efficiency scores):

Apply minimum episode criteria for health care providers to be used in correlation analysis.

For each health care provider, calculate an overall weighted average service and sub-service category score.

For each health care provider, create a medical condition-specific service and sub-service category score.

Calculate an overall weighted average procedure or service code score for each health care provider.

Calculate a medical condition-specific procedure or service code score for each health care provider.

If desired, remove outlier health care providers from analysis at a service category, sub-service category, and procedure or service code level.

Calculate the correlation to health care provider efficiency scores at each level described above using a Pearson's correlation calculation.

Correlated service and sub-service categories and procedures or services can be selected as MedMarkers and used to identify health care providers that meet a desired practice pattern.

These steps preferably occur after removing outlier episodes and health care providers that did not meet a minimum episode number established when running EfficiencyCare system. Therefore, outlier episodes identified during efficiency analysis, and health care providers not receiving an efficiency score, are not included in the analysis.

In one embodiment, a health care provider must have a minimum number of non-outlier episodes at the specialty-specific marketbasket level or medical condition level in order to be included in the correlation analysis. This minimum episode number should not be confused with a minimum episode number used to establish whether a health care provider receives an efficiency score.

In one embodiment, each health care provider's overall weighted average service category utilization per episode is divided by the peer group overall weighted average service category utilization per episode to calculate an overall service category score. Also, each health care provider's overall weighted average sub-service category utilization per episode is divided by the corresponding peer group's overall weighted average sub-service category utilization per episode to calculate an overall sub-service category score.

NOTE: Overall utilization rates for service and sub-service categories may be found in the EfficiencyCare system output file: Detail.tab.

In one embodiment, CPT-4 and HCPCS codes represent the procedure or service code level detail that is used to report services per episode rate for the health care provider and the peer group. The present invention uses this information at the overall weighted average level to calculate a unique procedure or service code score. Each health care provider's procedure or service code per episode rate is divided by the corresponding peer group procedure or service code per episode rate to calculate an overall procedure or service code score. For example, a dermatologist's overall skin biopsy rate per episode may be 0.477 services per episode. The peer group skin biopsy per episode rate is 0.175, resulting in a CPT-4 score for the dermatologist of a 0.477/0.175=2.72.

Similar to the overall weighted average service and sub-service category score, a medical condition-specific service category and sub-service category utilization score are calculated for each health care provider. Each health care provider's condition-specific service category utilization per episode is divided by the peer group service category utilization per episode to calculate a condition-specific service category score. Also, each health care provider's condition-specific sub-service category utilization per episode is divided by the corresponding peer group sub-service category utilization per episode to calculate a condition-specific sub-service category score.

NOTE: Medical condition-specific utilization rates for service and sub-service categories may be found in the EfficiencyCare system output file: Detail.tab.

In one embodiment, CPT-4 and HCPCS code detail may also be available for medical conditions within a market basket of interest. The condition-specific services per episode rate for the health care provider and the peer group may be used to calculate a service code score. For a specific medical condition, each health care provider's service code per episode rate is divided by the corresponding peer group condition-specific service code per episode rate to calculate a score. For example, a dermatologist's benign neoplasm of the skin biopsy rate per episode may be 0.500 services per episode. The peer group benign neoplasm of the skin biopsy rate per episode may be 0.250, resulting in a CPT-4 score for the dermatologist of a 0.500/0.250=2.00.

In the preferred embodiment health care provider outlier analysis is preferably performed after health care providers receive a service category score. The parameter SWITCH_BE_PROVOUTLIER in the run.ini configuration file defines the percent of health care providers that will be removed from correlation analysis in one embodiment of the present invention. Within each specialty marketbasket's service category, a percentage of health care providers with the greatest absolute variance between the health care provider's efficiency score and the service category score are removed from correlation analysis in this embodiment. The health care provider outlier analysis removes health care providers having differences that are far away from a major part of the data. One reason for removing them is that those health care provider outliers in the "difference area" may not be reliable from a statistical sense. Typically, the same health care providers are removed from sub-service category and procedure or service codes within the corresponding service category for both the overall marketbasket level and medical condition level correlation analysis. The health care providers included in the correlation analysis may differ by service category. For example, the health care provider outlier parameter default value may be 10%. Table 1 refers to a General Internist with an overall efficiency score of a 0.90, and demonstrates if this health care provider is to be included in correlation analysis for two separate service categories. In other embodiments, other health care provider outlier analysis methods may be utilized.

TABLE 1

General Internist Physician Outlier Example

| Service Category | Overall Efficiency Score | Service Category Score | Absolute Variance | Include Physician in Correlation Analysis? (includes corresponding sub-service category and procedure or service level correlation analysis) |
| --- | --- | --- | --- | --- |
| Diagnostic Tests | 0.90 | 2.50 | 1.60 | No. This physician is in the top 10% of physicians with greatest variance. |
| Medical/Surgical | 0.90 | 1.20 | 0.30 | Yes. This physician is not in the top 10% of physicians with the greatest variance. |

If the percent of health care providers removed as outliers cannot be achieved, then no health care providers are removed from the peer group in one embodiment of the present invention. For example, if there are 6 Allergists and 10% are to be removed, no health care providers are removed from the Allergist marketbasket for correlation analysis.

Peer group substitution is preferably used for health care providers who have passed the outlier criteria, but have not performed any services in a service category, sub-service category, or for a service code. Health care providers who did not receive a service category, sub-service category, or procedure or service code score because they did not perform those services or procedures will receive a score of a 1.0, which represents the peer group results. For example, if a health care provider did not perform any imaging tests, the health care provider's overall weighted average sub-service category score for imaging would preferably be substituted with a value of 1.0. In other embodiments, other peer group substitution methods may be utilized.

The main statistical analysis performed in one embodiment of the present invention is the Pearson's correlation analysis. Pearson's correlation analysis is used to calculate the correlation of a service category, sub-service category, or procedure or service code to health care provider efficiency score—Pearson's correlation coefficient (r). In the presentation of the correlation results, the correlation coefficient (r) indicates the strength and direction of a linear relationship between the dependant and independent variables, and varies from a low of −1.00 to a high of 1.00. The higher the absolute value of the coefficient, the stronger the relationship between the two variables. In health services research, two variables may be considered fairly correlated if "r" is greater than some limit (e.g., 0.20 or so). Also, two variables may be considered highly correlated if "r" is greater than some limit (e.g., 0.40 or so). Other statistical measurements are also within the scope of the present invention.

Correlation analysis is typically based on the identification of the dependent and independent variables which defines the detailed level for analysis.

Dependent variable. The dependent variable in the correlation model in the preferred embodiment of the present invention is a health care provider's efficiency score. The dependent variable is the health care provider's specialty-specific overall weighted average efficiency score if looking at the overall market basket level. The dependent variable is the health care provider's specialty-specific and medical condition-specific efficiency score if looking at the medical condition level.

Independent variables. There are three (3) types of independent variables that are included in the preferred embodiment of the present invention. These are listed in the following table.

TABLE 2

Potential Independent Variable Types

| Variable Types | Definition |
| --- | --- |
| Service Category Score | This is the service category score at either the overall marketbasket level or the medical condition-specific level. In one embodiment, there are 11 service categories. |
| Sub-Service Category Score | This is the sub-service category score at either the overall marketbasket level or the medical condition-specific level. In one embodiment, there are 21 sub-service categories. |
| Procedure or Service Code Score | This is a procedure or service code score at the overall marketbasket level or the medical condition-specific level. In one embodiment, the procedure or service code score is based on CPT-4 or HCPCS codes. |

The Pearson's correlation coefficient (r) is used in one embodiment of the present invention to determine the strength of the relationship between the health care provider efficiency score and health care provider service category, sub-service category, and service code score. This coefficient provides a numeric measure of the strength of the linear relationship between these two variables.

Pearson's correlation coefficient (r) ranges from a low of −1.00 to a high of 1.00. Positive correlations mean that the health care provider service category, sub-service category, and service code scores are positively associated with the health care provider efficiency score. That is, if a health care provider does more of the particular service code per episode as compared to the peer group, then the health care provider most often has an efficiency score greater than a 1.00. Vice versa, if a health care provider does less of the particular service code per episode as compared to the peer group, then the health care provider most often has an efficiency score less than a 1.00. Therefore, a positively correlated service code indicates that health care providers performing more of this service code tend to have more inefficient practice patterns as compared to the peer group. Negative correlations mean that the health care provider service category, sub-service category, and service code scores are negatively associated with the health care provider efficiency score. That is, if a health care provider does more of the particular service code per episode as compared to the peer group, then the health care provider most often has an efficiency score less than a 1.00. Vice versa, if a health care provider does less of the particular service code per episode as compared to the peer group, then the health care provider most often has an efficiency score greater than a 1.00. Therefore, a negatively correlated service code indicates that health care providers performing more of this service code tend to have more efficient practice patterns as compared to the peer group. Note that Pearson's correlation coefficient is used in one embodiment of the present invention and is used here as an example of a measure of correlation. Other measures of correlation are also within the scope of the present invention.

TABLE 3

Potential Correlation Intervals in Relation to Efficiency

| Correlation Range | Correlation to Efficiency or Inefficiency |
| --- | --- |
| >0.40 | High positive correlation to health care provider efficiency scores; the more he does, the more likely the health care provider is to receive an inefficient score. |
| 0.20 to 0.40 | Good positive correlation to health care provider efficiency scores |
| −0.20 to 0.20 | Low to no correlation to health care provider efficiency scores |
| −0.20 to −0.40 | Good negative correlation to health care provider efficiency scores |
| <−0.40 | High negative correlation to health care provider efficiency scores; the more he does, the more likely the health care provider is to receive an efficient score. |

FIG. 1 is a graph showing a Positive Correlation Example. In this FIG., each procedure score for skin biopsies (CPT-4 11100) has been plotted against each dermatologist's overall health care provider efficiency score. When the CPT-4 score is high, the health care provider efficiency score is high. Alternatively, when the CPT-4 score is low, the overall efficiency score is low, resulting in a high Pearson's correlation coefficient of a 0.64. According to Table 3 (above)—Potential Correlation Intervals in Relation to Efficiency, in this population, skin biopsies have a high positive correlation to health care provider efficiency scores, indicating a health care provider doing more of this procedure is more likely to receive an inefficient score.

Figure 2:
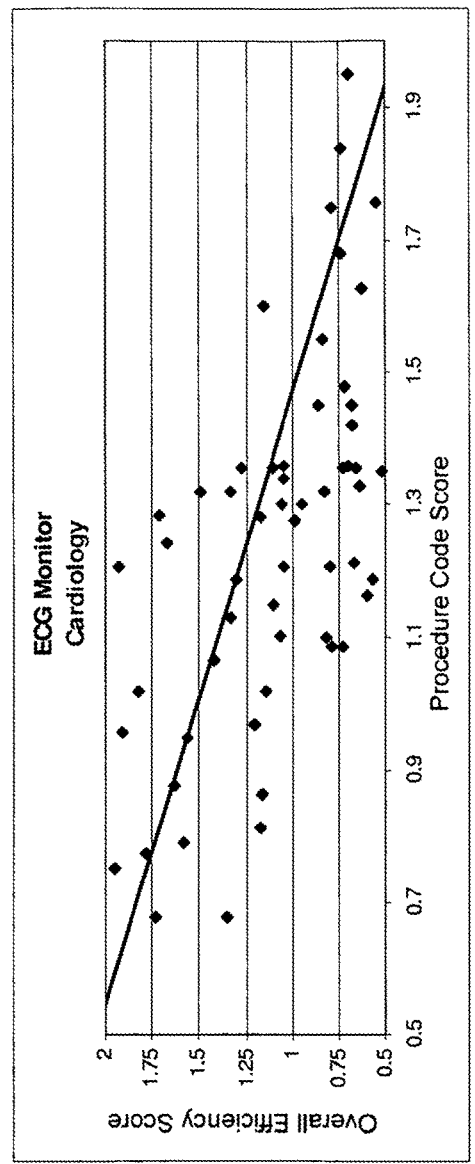
FIG. 2 is a graph showing a Negative Correlation Example.

FIG. 2 is a graph showing a Negative Correlation Example. In this FIG., each procedure score for ECG Monitoring (CPT-4 93325) has been plotted against each Cardiologists' overall health care provider efficiency score. In this example, when the procedure score for ECG Monitoring (CPT-4 93325) for Cardiologists is high, the health care provider efficiency score is low. This is the opposite of the skin biopsy pattern shown above. When the CPT-4 score is low, the overall efficiency score is high, resulting in a negative Pearson's correlation coefficient of a −0.26. According to Table 3 (above)—Potential Correlation Intervals in Relation to Efficiency, in this population, ECG Monitoring has a good negative correlation to health care provider efficiency scores, indicating a health care provider doing more of this procedure is more likely to receive an efficient score.

A MedMarker is preferably a CPT-4 or HCPCS code that is relatively correlated to the health care provider efficiency score. To qualify as a MedMarker, the procedure or service should preferably have the following properties:

Good correlation (using Pearson's correlation "r" in this example) to a health care provider specialty type's overall or medical condition-specific efficiency score;

A higher prevalence rate per overall weighted average episode of care, or medical condition-specific episode of care.

Clinical relevance in terms of medical support literature as to when service should be performed; and A reasonable charge per service (e.g., $50-to-$400 per service in this example). The health care provider's condition-specific efficiency score is a reflection of the services used to treat a specific medical condition as compared to an immediate peer group.

More than a given percentage of the health care providers (within the specialty type of interest) perform one or more of the service code of interest.

The present invention allows an organization to identify one main practice pattern per specialty type per region that is most associated with health care provider efficiency scores, and identify those health care providers who meet this practice pattern.

Identify a MedMarker (or several MedMarkers) that will be used to establish a practice pattern for specialty-specific health care providers in a given region (see FIG. 4). Users can select positively or negatively correlated MedMarkers (see FIG. 1 & FIG. 2).

For the MedMarkers selected, define the percentage above or below the services per episode rate to identify health care providers with a specified practice pattern. For example, for MRI of the lumbar region (CPT-4 72148), a general internist's service per episode rate should be 10% higher than the peer group rate for the health care provider to be defined as meeting the practice pattern (see FIG. 5).

When selecting multiple MedMarkers to establish a practice pattern, a threshold can be set for the amount of MedMarkers that must meet or exceed the services per episode rate. For example, if 7 MedMarkers are used to establish a practice pattern, a user may only require 5 out of 7 MedMarker services per episode rate be met in order to identify a health care provider as matching a specified practice pattern (see FIG. 5).

The present invention will preferably produce a list of Provider IDs that match the identified practice pattern (see FIG. 5). The Provider ID list produced by the present invention can be loaded into EfficiencyCare Practitioner Efficiency Reports to further drill down on their practice patterns.

FIGS. 6 through 8 are diagrams illustrating the process of identifying MedMarkers, in accordance with one embodiment of the present invention. These examples are exemplary, and are only included here for illustrative purposes. It should be understood that these functions are automated in a computer system in a preferred embodiment of the present invention, and the separate reports are shown merely to illustrate the process.

FIG. 6 is an exemplary Practitioner Efficiency Report, in accordance with one embodiment of the present invention. It contains episode information for one practitioner (i.e. health care provider) for a number of medical conditions. For each medical condition, as well as a weighted average of all such medical conditions, averages for a peer group of health care providers are also shown. For each medical condition and weighted average, there are a number of columns. It shows the average charges per episode of care. The first column shows the name of the medical condition. The next shows a Severity of Illness (SOI) level for the condition. This is followed by an episode count and average charger per episode. Then, the average charge per episode is broken down across service categories in columns for: professional visits; diagnostic tests; lab/pathology; medical/ surgical; prescriptions (Rx); facility outpatient; facility hospital; alternate sites; and other medical expenses. An efficiency score is computed for the practitioner by dividing his average charge per episode of his average weighted charges by the average charge per episode for the peer group. In this case, the average charge per episode for this practitioner was $567, and for the peer group, it was $399. The quotient of these two average charges is 1.42, which can be utilized as an efficiency measurement. Other methods of and techniques for computing an efficiency measurement or score for health care providers are also within the scope of the present invention. In comparing this health care provider with others, this efficiency rating is in the $4^{th}$ quartile, or $10^{th}$ decile. A question is asked, what CPT-4 code is most associated with the efficiency score? There are several steps outlined below to answer this question. The first step is to identify a service category where the health care provider has significantly higher overall weighted average charges than the peer group. In this example, medical/surgical overall weighted average charge for the health care provider is significantly higher than the overall weighted average charge for the peer group as indicated by the asterisk on the practitioner weighted average result for Med/Surg, and is circled to illustrate this.

A next step is to drill-down to the service code level under sub-service ambulatory surgical procedures to identify health care provider service codes with higher per episode rates than the peer group. FIG. 7 is an exemplary Service Prevalence Report in accordance with the example shown in FIG. 6. For the Dermatology specialty the report contains information on services ordered for one healthcare provider and the peer group. The report also shows the number of unique episodes for the healthcare provider and the peer group as well as the number of unique healthcare providers in the peer group. Also, for both the healthcare provider and the peer group, the number of services, number of services per episode, and the charge per service is shown for each service listed. There is also a column showing services per episode percent difference from the peer group.

Next, there is also a CPT-4 table shown in FIG. 7 (in the upper right hand quadrant) for CPT-4 11100. In the CPT-4 11100 table, the overall efficiency scores of several healthcare providers are shown for this CPT-4 code (biopsy, skin lesion). In one embodiment, it would contain entries for each healthcare provider in the peer group having treated a sufficient number of episodes in the Dermatology marketbasket of medical conditions. Also, a CPT-4 score is calculated for this CPT-4 code by dividing a healthcare provider number of services per episode by an average value for his peer group. The CPT-4 score for each healthcare provider in the table is included in a CPT-4 score column along side his efficiency score. In the case of the first Dermatologist in the table, overall efficiency score is 1.42, and the first Dermatologist has a CPT-4 score of 2.73. In one embodiment, this type of CPT-4 table is generated for each CPT-4 code being evaluated as a potential MedMarker. After the CPT-4 table is populated for a CPT-4 code, a statistical measurement, such as a correlation coefficient (e.g. Pearson's "r"), is computed for the pairs of efficiency scores and CPT-4 scores for each row in the table. In one embodiment, a Pearson's coefficient is the statistical measurement calculated. In other embodiments, other measures of correlation or other statistical measurements may be utilized.

Finally, to identify the CPT-4 code most associated with efficiency scores for the Dermatologists, FIG. 8 provides an exemplary Procedure Code Report for the Dermatology specialty type, in accordance with the invention and example shown in FIG. 7. This report shows one line for each CPT-4 code being evaluated as a potential MedMarker for the given sub-service category of ambulatory surgical services. One example is the Pearson's correlation computed for CPT-4 11100 shown in FIG. 7. The first column in the report contains the statistical measurement (e.g. Pearson's correlation coefficient) calculated for pairs of efficiency scores and CPT-4 scores for that CPT-4 code. The second column contains the corresponding CPT-4 procedure code. This is followed by columns for a short name for the CPT-4 code, an average rate per episode for this code, and an average cost per procedure. The CPT-4 codes with sufficiently high positive or negative correlations are considered as MedMarkers. In this FIG. 8, CPT-4 procedure 11100 has a correlation of 0.289, 11101 has a correlation of 0.218, 11401 has a correlation of 0.302, and 11402 has a correlation coefficient of 0.221. These all have a correlation coefficient greater than 0.2, which is a exemplary cutoff in one implementation of the present invention, and these services, therefore, may be considered as potential MedMarkers. They all have a relatively high correlation between efficiency scores and CPT-4 scores. The remainder of the CPT-4 codes listed for this sub-service category have lower correlation coefficients, are thus less correlated, and are preferably eliminated from consideration as potential MedMarkers.

The MedMarker information presented in FIG. 8 is for sub-service category of ambulatory surgical services across all medical conditions in the Dermatology marketbasket. In one embodiment, MedMarkers can be identified across all sub-service category services for a given medical condition (see FIG. 3) FIG. 3 is an exemplary Sub-Service Detail Correlation Report, in accordance with one embodiment of the present invention. This report shows the correlation between different services and health care provider efficiency for a specialty (in this example, General Internist) and a specific medical condition (in this example, Low back pain). The fields in this report are:

| Field Name | Notes |
|---|---|
| Top of Report | |
| Marketbasket | This is the name of the specialty-specific marketbasket selected for analysis. |
| SOI - Medical Condition | A specialty-specific marketbasket consists of the common medical conditions treated by each specialty type. This field presents the medical condition name and the severity-of-illness (SOI) being examined. There are up to three SOI levels for each medical condition, with SOI-1 being the least severe (routine, non-complicated), and SOI-3 being the most severe SOI (severity of illness). |

-continued

| Field Name | Notes |
|---|---|
| Aggregate Group | Marketbasket System output contains information organized by aggregate groups that users define. This is the name of the aggregate group relevant to the current data run. |
| Correlation Cutoff | This is the cutoff value used to determine what procedures or services to display on the Sub-Service Detail Report. This parameter is not applicable for the service category and sub-service category level reports. |

Body of Report
Columns

| | |
|---|---|
| 🛒 | This column allows you to select the MedMarkers of interest to add to a user's BullsEye "shopping cart". Any service category or sub-service category row can be selected by checking the box under this column. |
| Corr | This column presents the correlation results of the service categories or sub-service categories to the health care provider's efficiency scores at the overall marketbasket level or the medical condition level within a marketbasket. |
| Service/Sub-Service Category | This column presents the name of the 11 service categories or 21 sub-service categories. |
| Number Services | This column presents the total number of services for the specialty-specific peer group at the overall marketbasket level or the medical condition level within a marketbasket. |
| Service Units | This column presents the type of service associated with each service category or sub-service category. For example, "Professional Visits" service type is office visits. |
| Services per Episode | This column presents the average number of services per episode for the specialty-specific peer group at the overall marketbasket level or the medical condition level. |
| Charge per Service | This column presents the average charge per service for the specialty-specific peer group at the overall marketbasket level or the medical condition level within a marketbasket. |
| Unique Practitioners | This column presents the number of health care providers in the specialty-specific peer group at the overall marketbasket level or the medical condition level within a marketbasket. |
| Performing Practitioners | This column presents the percentage of the health care providers in the peer group having performed the service at least once at the overall marketbasket or the medical condition level. |

As defined earlier in discussion of FIG. 5, FIG. 4 shows an exemplary MedMarker Checkout Report, in accordance with the embodiment shown in FIG. 3. This report is a subset of the report shown in FIG. 3, with columns from that report selected by clicking under the marketbasket icon (🛒) in the first column.

FIG. 5 shows a MedMarker Target Report, in accordance with the embodiment shown in FIG. 4 as discussed earlier. A user first selects a number of services as show in FIG. 4 by clicking under the marketbasket icon (i) in FIG. 3. The user then selects how many of the marketbasket services are required for a health care provider in this report (the report shown requires one of the three) and a threshold based on the peer group. The report generated lists the practitioners who qualify under these criteria. The fields in this report are:

| Field Name | Notes |
|---|---|

Top of Report

| Aggregate Group | Marketbasket System output contains information organized by aggregate groups that you define. This is the name of the aggregate group relevant to the current data run. |
|---|---|
| Marketbasket | This is the name of the specialty-specific marketbasket selected for analysis. A specialty-specific marketbasket consists of the common medical conditions treated by each health care provider specialty type. This field presents the medical condition name being examined. If analysis is performed at the marketbasket level, this field will contain the value "all". |
| Medical Condition | |
| SOI | This field presents the severity-of-illness (SOI) being examined. There are up to three SOI levels for each medical condition, with SOI-1 being the least severe (routine, non-complicated), and SOI-3 being the most severe SOI (severity of illness). If analysis is performed at the Marketbasket level, this field will be blank. |

Body of Report
Columns

| Practitioner ID | This is the unique identification number assigned to the health care provider analyzed. |
|---|---|
| Practitioner Name | This is the name of the health care provider analyzed. |
| Efficiency Score | This is the efficiency score for each health care provider. At the marketbasket level, the efficiency score is calculated by dividing the health care provider's weighted average overall charges by the specialty-specific peer group's weighted average overall charges. At the medical condition-SOI level, the efficiency score is calculated by dividing the health care provider's average medical condition-SOI charges by the specialty-specific peer group's average medical condition-SOI charges within a marketbasket. |
| MedMarkers Meeting Criteria | This column presents the number of MedMarker criteria met by each health care provider. |

A Practitioner MedMarker Report (not shown) provides users with additional detailed information for each health care provider displayed in the MedMarker Target Report shown in FIG. 5. The MedMarker Target report has links for each practitioner, and when that link is selected, the details for each of the selected MedMarkers is shown for that practitioners.

Figure 9:
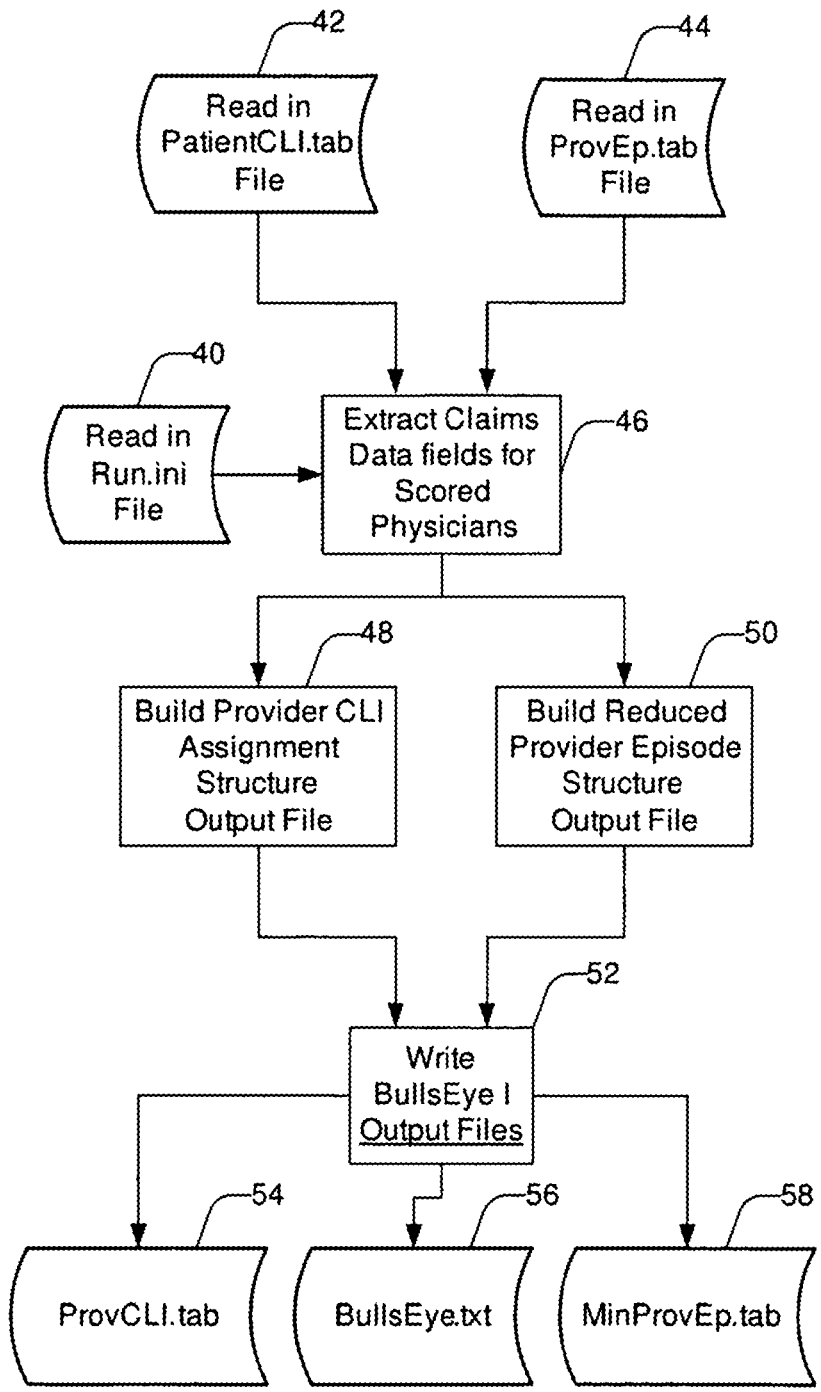
FIGS. 9 and 10 are flowcharts illustrating exemplary operation of one embodiment of the present invention.
Figure 10:
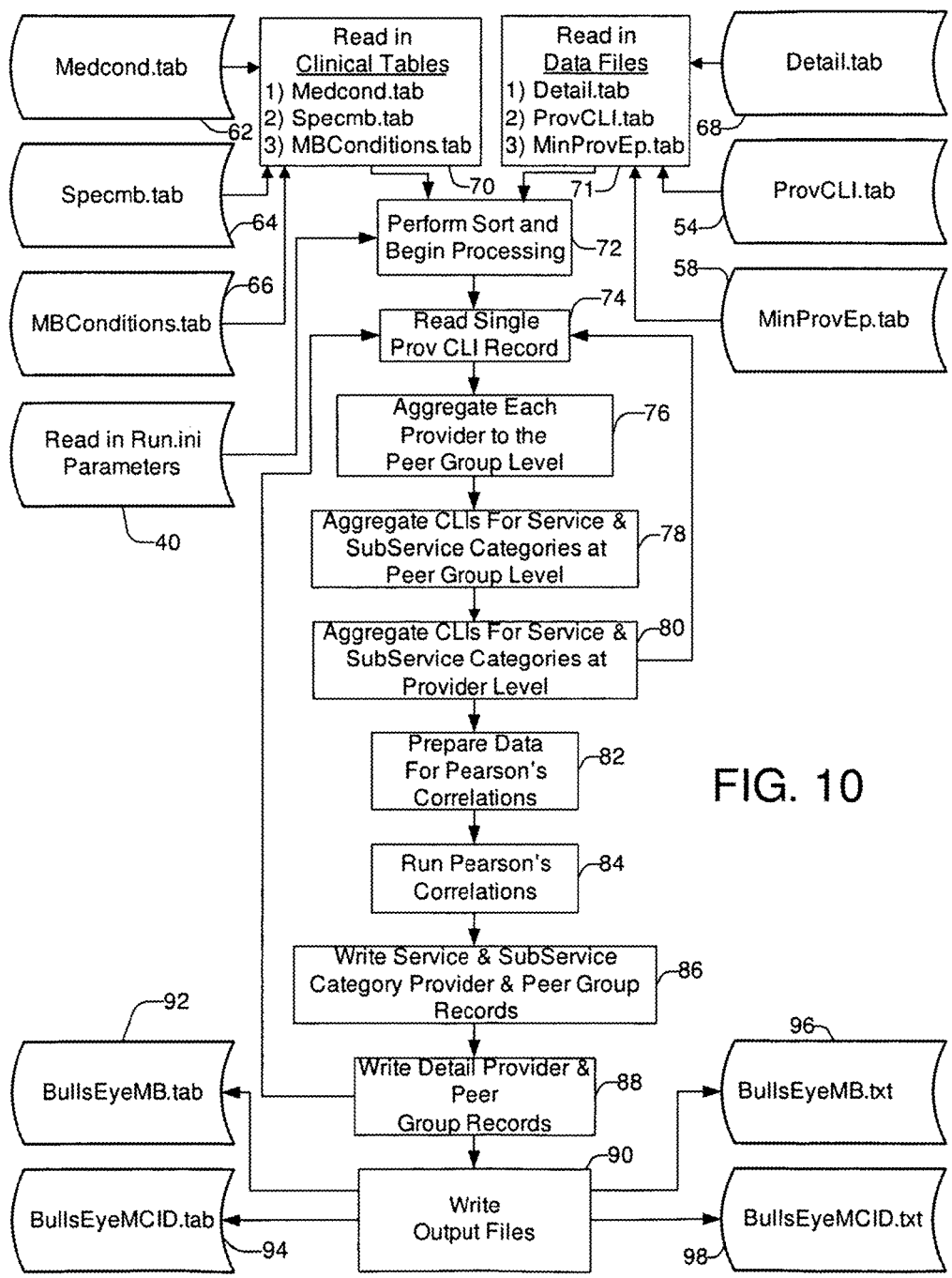

FIGS. 9 and 10 are flowcharts illustrating exemplary operation of one embodiment of the present invention. They are separated into two flowcharts for illustrative purposes, and it should be understood that they may not be separate in different embodiments. Furthermore, files are shown in these flowcharts. It should be understood this is illustrative and that other methods and techniques of data organization and management are also within the scope of the present invention. For example, many of the operations shown may be implemented through database operations in place of file operations.

FIG. 9 starts by reading in a PatientCLI file 42, a ProvEp file 44, and Run.ini parameters 40. From these files, claims data fields are extracted for scored health care providers, step 46. From this, a Provider CLI assignment structure file is built, step 48, and a Reduced Provider Episode Structure Output file is built, step 50. Then, the first phase of files are written, step 50, including a ProvCLI file 54, a BullsEye file 56, and a MinProvEp file 58.

FIG. 10 starts by reading in clinical tables, step 70 from a MedCond file 62, Specmb file 64, and MBConditions file 66. Also, data files are read in, step 68, including: a Detail file 68; the ProvCLI file 54; and the MinProvEp file 58. The Run.ini run time parameters 40 are read in, and a sort is performed, step 72. A loop is entered, starting with reading a single ProvCLI record, step 74. Health care providers are aggregated to the peer group level, step 76. Claim Line Items are aggregated for service and subservice categories at the peer group level, step 78 and at the provider level, step 80. An inner loop repeats for each CLI record, step 74. Then, data is prepared for statistical analysis, step 80, and statistical analysis, such as Pearson's correlation, is performed, step 84. Service and subservice category provider and peer group records are written, step 86, and provider and peer group records are written, step 88. An outer loop then repeats, starting at the beginning of the CLI records, step 74. At the end of the outer loop, the output files are written, step 90, including: a BullsEyeMB.tab file 92; a BullEyeMCID.tab file 94; a BullsEyeMB.txt file 96; and a BullsEyeMCID.txt file 98.

Figure 11:
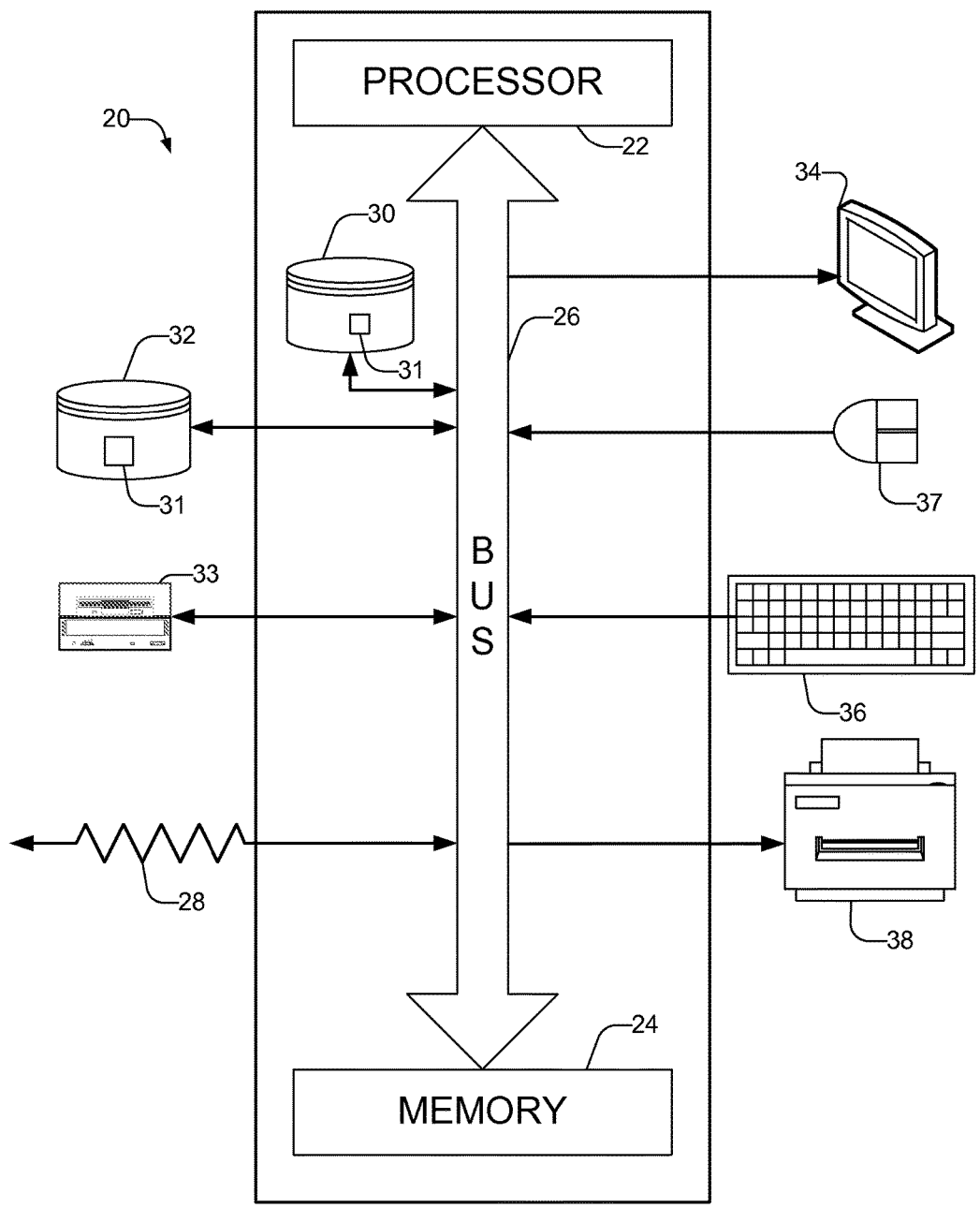
FIG. 11 is a block diagram illustrating a General Purpose Computer, such as utilized to implement the present invention, as shown in FIGS. 9 and 10.

FIG. 11 is a block diagram illustrating a General Purpose Computer, such as utilized to implement the present invention, as shown in FIGS. 9 and 10. The General Purpose Computer 20 has a Computer Processor 22 (CPU), and Memory 24, connected by a Bus 26. Memory 24 is a relatively high speed machine readable medium and includes Volatile Memories such as DRAM, and SRAM, and Non-Volatile Memories such as, ROM, FLASH, EPROM, EEPROM, and bubble memory. Also connected to the Bus are Secondary Storage 30, External Storage 32, output devices such as a monitor 34, input devices such as a keyboard 36 with a mouse 37, and printers 38. Secondary Storage 30 includes machine-readable media such as hard disk drives, magnetic drum, and bubble memory. External Storage 32 includes machine-readable media such as floppy disks, removable hard drives, magnetic tape, CD-ROM, and even other computers, possibly connected via a communications line 28. The distinction drawn here between Secondary Storage 30 and External Storage 32 is primarily for convenience in describing the invention. As such, it should be appreciated that there is substantial functional overlap between these elements. Computer software such operating systems, utilities, user programs, and software to implement the present invention and data files can be stored in a Computer Software Storage Medium, such as memory 24, Secondary Storage 30, and External Storage 32. Executable versions of computer software 33, such as software utilized to implement the present invention can be read from a Non-Volatile Storage Medium such as External Storage 32, Secondary Storage 30, and Non-Volatile Memory and loaded for execution directly into Volatile Memory, executed directly out of Non-Volatile Memory, or stored on the Secondary Storage 30 prior to loading into Volatile Memory for execution.

Those skilled in the art will recognize that modifications and variations can be made without departing from the spirit of the invention. Therefore, it is intended that this invention encompass all such variations and modifications as fall within the scope of the appended claims.

What is claimed is:

1. A computer-implemented method of identifying a practice pattern associated with an efficiency of medical care providers, said method comprising:

providing, at a computer system, a plurality of episodes of care records, wherein each of the plurality of episodes of care records is identified by one of a plurality of episode-of-care identifiers, and includes one of a plurality of provider identifiers identifying one of a plurality of medical care providers, wherein an episode metric is defined as at least one of an average utilization per episode of care and an average cost per episode of care;

providing, at the computer system, a plurality of patient treatment claim records, wherein each of the plurality of patient treatment claim records includes (i) an associated one of the episode-of-care identifiers, and (ii) at least one of a plurality of codes, each of the plurality of codes associated with at least one of a procedure and service in a medical care field associated with the plurality of medical care providers, each of the plurality of codes being assigned to one of a plurality of service categories;

providing, at the computer system for each of the plurality of medical care providers, a provider service category episode metric for each of the service categories, the provider service category episode metric being the episode metric for the respective provider across the codes in the respective service category;

providing, at the computer system, a group service category episode metric for each of the service categories, the group service category episode metric being the episode metric across the codes in the respective service category across all of the providers;

providing, at the computer system, a plurality of medical care provider overall efficiency measurements each associated with one of the plurality of provider identifiers;

displaying, to a user, a practitioner efficiency report associated with a first one of the plurality of medical care providers, wherein the practitioner efficiency report includes (i) the overall efficiency measurement associated with the first medical care provider, (ii) the provider service category episode metric of the first medical care provider for each of the service categories, (iii) the group service category episode metric for each of the service categories, and (iv) a graphical indication for at least one of the service categories that the indicated provider service category episode metric exceeds the corresponding group service category episode metric by a first threshold amount;

receiving, from the user, a designation of one of the at least one graphically indicated service categories for a drill-down analysis;

providing, at the computer system, for each of the plurality of medical care providers, a provider code episode metric for each of the codes associated with the designated service category, the provider code episode metric being the episode metric for the respective provider for the respective code;

providing, at the computer system a group code episode metric for each of the codes associated with the designated service category, the group code episode metric being the episode metric across all providers for the respective code;

associating, by the computer system, with each of the plurality of medical care providers, a code score for each of the codes associated with the designated service category, wherein the code score is based on (i) the provider code episode metric for the respective code and the respective provider relative to (ii) the group code episode metric for the respective code;

calculating, for each of the codes associated with the designated service category, a correlation value based on a plurality of pairs of values, each pair of values corresponding to a respective one of the plurality of medical providers and comprising:
the overall efficiency measurement associated with the respective medical care provider, and
the code score associated with the respective code for the respective medical care provider;

displaying, to the user, a code report for the designated service category, wherein the code report includes (i) an identifier of at least a portion of the codes in the designated service category, (ii) the correlation value corresponding to each included code, and (iii) a graphical indication of at least one of the included codes as having an associated correlation value exceeding a second threshold amount;

receiving, from the user, a designation of a set of the included codes as the practice pattern associated with efficiency; and displaying, to the user, a practitioner target report, wherein the practitioner target report includes (i) a respective identifier of each of a subset of the plurality of medical providers, (ii) an identifier of a number of the designated codes in the practice pattern for which the provider code episode metric of the respective identified provider exceeds the group code episode metric by a third threshold amount, and (iii) for each identified provider, a link to a detail display of the provider code episode metrics of the respective identified provider for the included codes in the practice pattern.

2. The method in claim 1 further comprising:
calculating the correlation value at a plurality of levels of aggregation of medical care information from the patient treatment claim records.

3. The method in claim 2 wherein:
the plurality of levels includes aggregation by specific medical conditions, and the code score for each of the codes associated with the designated service category is based on the provider code episode metric for the respective medical care provider for episode-of-care identifiers associated with each specific medical condition relative to the group code episode metric for episode-of-care identifiers associated with the specific medical condition.

4. The method in claim 1 which further comprises:
computing a second statistical analysis from aggregated medical care information on the computer system;
generating peer group level results utilizing the second computed statistical analysis on the computer system; and
generating medical care provider level results utilizing the second computed statistical analysis on the computer system; and
calculating the medical care provider overall efficiency measurement through a comparison of medical care provider level results to peer group level results on the computer system.

5. The method in claim 1 wherein the code score associated with each of the codes associated with the designated service category is based on the utilization for each of the codes.

6. The method in claim 5 wherein the utilization is a utilization frequency rate.

7. The method in claim 1, wherein displaying the practitioner target report comprises displaying the subset of providers each having an overall efficiency score exceeding a fourth threshold amount.

8. The method in claim 1 which further comprises:
removing medical care providers failing to meet a minimum unit of analysis criteria before calculating the correlation value.

9. The method in claim 8 wherein:
the minimum unit of analysis is determined by a configuration parameter.

10. The method in claim 1 wherein the correlation calculation includes a Pearson's correlation.

11. The method in claim 1 which further comprises:
selecting statistically related medical care information to identify medical care providers meeting the identified practice pattern based on the selected indicators on the computer system.

12. A computer system for identifying a practice pattern associated with an efficiency of medical care providers, said computer system comprising:
a processor capable of executing computer instructions;
a memory coupled to the processor containing computer instructions for:
accessing a plurality of episodes of care records, wherein each of the plurality of episodes of care records is identified by one of a plurality of episode-of-care identifiers, and includes one of a plurality of provider identifiers identifying one of a plurality of medical care providers, wherein an episode metric is defined as at least one of an average utilization per episode of care and an average cost per episode of care;
accessing a plurality of patient treatment claim records, wherein each of the plurality of patient treatment claim records includes (i) an associated one of the episode-of-care identifiers, and (ii) at least one of a plurality of codes, each of the plurality of codes associated with at least one of a procedure and service in a medical care field associated with the plurality of medical care providers, each of the plurality of codes being assigned to one of a plurality of service categories;
accessing, for each of the plurality of medical care providers, a provider service category episode metric for each of the service categories, the provider service category episode metric being the episode metric for the respective provider across the codes in the respective service category;
accessing a group service category episode metric for each of the service categories, the group service category episode metric being the episode metric across the codes in the respective service category across all of the providers;
accessing a plurality of medical care provider overall efficiency measurements each associated with one of the plurality of provider identifiers;
displaying, to a user, a practitioner efficiency report associated with a first one of the plurality of medical care providers, wherein the practitioner efficiency report includes (i) the overall efficiency measurement associated with the first medical care provider, (ii) the provider service category episode metric of the first medical care provider for each of the service categories, (iii) the group service category episode metric for each of the service categories, and (iv) a graphical indication for at least one of the service categories that the indicated provider service category episode metric exceeds the corresponding group service category episode metric by a first threshold amount;
receiving, from the user, a designation of one of the at least one graphically indicated service categories for a drill-down analysis;
accessing, for each of the plurality of medical care providers, a provider code episode metric for each of the codes associated with the designated service category, the provider code episode metric being the episode metric for the respective provider for the respective code;
accessing a group code episode metric for each of the codes associated with the designated service category, the group code episode metric being the episode metric across all providers for the respective code;

associating, with each of the medical care providers, a code score for each of the codes associated with the designated service category, wherein the code score is based on (i) the provider code episode metric for the respective code and the respective provider relative to (ii) the group code episode metric for the respective code;

calculating, for each of the codes associated with the designated service category, a correlation value based on a plurality of pairs of values, each pair of values corresponding to a respective one of the plurality of medical providers and comprising:
the overall efficiency measurement associated with the respective medical care provider, and
the code score associated with the respective code for the respective medical care provider;

displaying, to the user, a code report for the designated service category, wherein the code report includes (i) an identifier of at least a portion of the codes in the designated service category, (ii) the correlation value corresponding to each included code, and (iii) a graphical indication of at least one of the included codes as having an associated correlation value exceeding a second threshold amount;

receiving, from the user, a designation of a set of the included codes as the practice pattern associated with efficiency; and displaying, to the user, a practitioner target report, wherein the practitioner target report includes (i) a respective identifier of each of a subset of the plurality of medical providers, (ii) an identifier of a number of the designated codes in the practice pattern for which the provider code episode metric of the respective identified provider exceeds the group code episode metric by a third threshold amount, and (iii) for each identified provider, a link to a detail display of the provider code episode metrics of the respective identified provider for the included codes in the practice pattern.

13. A non-transitory recordable medium containing computer instructions for identifying a practice pattern associated with an efficiency of medical care providers, said computer instructions when executed by at least one processor cause the at least one processor to:

access a plurality of episodes of care records, wherein each of the plurality of episodes of care records is identified by one of a plurality of episode-of-care identifiers, and includes one of a plurality of provider identifiers identifying one of a plurality of medical care providers, wherein an episode metric is defined as at least one of an average utilization per episode of care and an average cost per episode of care;

access a plurality of patient treatment claim records, wherein each of the plurality of patient treatment claim records includes (i) an associated one of the episode-of-care identifiers, and (ii) at least one of a plurality of codes, each of the plurality of codes associated with at least one of a procedure and service in a medical care field associated with the plurality of medical care providers, each of the plurality of codes being assigned to one of a plurality of service categories;

access, for each of the plurality of medical care providers, a provider service category episode metric for each of the service categories, the provider service category episode metric being the episode metric for the respective provider across the codes in the respective service category;

access a group service category episode metric for each of the service categories, the group service category episode metric being the episode metric across the codes in the respective service category across all of the providers;

access a plurality of medical care provider overall efficiency measurements each associated with one of the plurality of provider identifiers;

display, to a user, a practitioner efficiency report associated with a first one of the plurality of medical care providers, wherein the practitioner efficiency report includes (i) the overall efficiency measurement associated with the first medical care provider, (ii) the provider service category episode metric of the first medical care provider for each of the service categories, (iii) the group service category episode metric for each of the service categories, and (iv) a graphical indication for at least one of the service categories that the indicated provider service category episode metric exceeds the corresponding group service category episode metric by a first threshold amount;

receiving, from the user, a designation of one of the at least one graphically indicated service categories for a drill-down analysis;

access, for each of the plurality of medical care providers, a provider code episode metric for each of the sets of related codes associated with the designated service category, the provider code episode metric being the episode metric for the respective provider for the respective code;

accessing a group code episode metric for each of the codes associated with the designated service category, the group code episode metric being the episode metric across all providers for the respective code;

associate, with each of the plurality of medical care providers, a code score for each of the codes associated with the designated service category, wherein the code score is based on (i) the provider code episode metric for the respective code and the respective provider relative to (ii) the group code episode metric for the respective code;

calculate, for each of the codes associated with the designated service category, a correlation value based on a plurality of pairs of values, each pair of values corresponding to a respective one of the plurality of medical providers and comprising:
the overall efficiency measurement associated with the respective medical care provider, and
the codes score associated with the respective code for the respective medical care provider;

display, to the user, a code report for the designated service category, wherein the code report includes (i) an identifier of at least a portion of the codes in the designated service category, (ii) the correlation value corresponding to each included code, and (iii) a graphical indication of at least one of the included codes as having an associated correlation value exceeding a second threshold amount;

receive, from the user, a designation of a set of the included codes as the practice pattern associated with efficiency- and display, to the user, a practitioner target report, wherein the practitioner target report includes (i) a respective identifier of each of a subset of the plurality of medical providers, (ii) an identifier of a number of the designated codes in the practice pattern for which the provider code episode metric of the respective identified provider exceeds the group code episode metric by a third threshold amount, and (iii) for each identified provider, a link to a detail display of the provider code episode metrics of the respective identified provider for the included codes in the practice pattern.

14. The method in claim 1 wherein providing the plurality of medical care provider overall efficiency measurements includes providing the plurality of medical care provider overall efficiency measurements wherein each overall efficiency measurement represents an average usage of resources per episode of care for the associated medical care provider relative to the average usage of resources per episode of care for the plurality of medical care providers, and wherein the average usage of resources per episode of care is weighted according to a predetermined relevance of an associated medical condition in a practice area associated with the plurality of medical care providers.

* * * * *